United States Patent [19]

Stewart et al.

[11] Patent Number: 5,807,802
[45] Date of Patent: Sep. 15, 1998

[54] STABLE AQUEOUS DISPERSIONS OF DIBUTYLTIN OXIDE

[75] Inventors: RoseMarie E. Stewart, Chicago, Ill.; Harold Mark, Fairfield, Conn.; Oliver Schumacher, Werne; Ulrich Stewen, Schwerte, both of Germany

[73] Assignee: Witco Corporation, Greenwich, Conn.

[21] Appl. No.: 679,270

[22] Filed: Jul. 12, 1996

[51] Int. Cl.[6] ............................. B01J 31/00; B32B 5/16; A61K 7/46
[52] U.S. Cl. ....................... 502/152; 508/527; 428/323; 512/3; 510/421
[58] Field of Search ........................... 502/152; 508/527; 510/517, 421, 445, 463, 506; 428/323; 512/3

[56] References Cited

U.S. PATENT DOCUMENTS 5,176,804  1/1993  Buttner et al. .......................... 204/499

FOREIGN PATENT DOCUMENTS 4303787     3/1994  Germany.
WO 93/09206 5/1993  WIPO.

OTHER PUBLICATIONS

Chemical Abstract: 109:192294.
Chemical Abstract: 96:69881.
Chemical Abstract: 115:73250.
Chemical Abstract: 90:72612.
Chemical Abstract: 107:200446.

*Primary Examiner*—Glenn A. Caldarola
*Assistant Examiner*—Tanaga A. Boozer
*Attorney, Agent, or Firm*—Scully, Scott Murphy & Presser

[57] ABSTRACT

Disclosed are aqueous dispersions of dibutyltin oxide which contain water, dibutyltin oxide in substantial amounts on the order of 50 to 75 wt. %, as well as a fatty acid ethoxylate surfactant, a suspending agent, and a viscosity modifier component of one or more $C_{12}$–$C_{24}$ fatty acids and/or alkali metal salts thereof.

21 Claims, No Drawings

STABLE AQUEOUS DISPERSIONS OF DIBUTYLTIN OXIDE

FIELD OF THE INVENTION

The present invention relates to compositions containing dibutyltin oxide (referred to herein as DBTO). The present invention relates more particularly to aqueous dispersions wherein the dibutyltin oxide component represents a substantial portion, e.g. over 50 wt. % of the dispersion, yet the dibutyltin oxide remains uniformly and homogeneously dispersed for extended periods of time and exhibits a controlled viscosity such that the dispersion is sufficiently fluid to be capable of being poured and pumped.

BACKGROUND OF THE INVENTION

Dibutyltin oxide is an established specialty chemical having a number of uses. For instance, dibutyltin oxide is used worldwide as a catalyst in the electrophoretic deposition of paint for the automobile industry.

It has been the practice to employ dibutyltin oxide as a solid, generally subdivided to the consistency of powder or finer-sized particles. Unfortunately, dibutyltin oxide in this solid form presents a number of drawbacks. The very fine particle size includes a certain portion of ultra fine powder and dust, which can pose environmental hazards to workers and equipment requiring special handling techniques and special equipment. In addition, the loss of solid dibutyltin oxide as dust and the like represents a loss of product which represents an economic loss to the user. The problems associated with the very fine particle size of solid dibutyltin oxide are thus borne in the manufacture, packaging, and use of dibutyltin oxide.

It is thus an object of the present invention to provide compositions containing major amounts of dibutyltin oxide, wherein the problems associated with the very finely divided solid form of dibutyltin oxide are avoided. The approach taken by the present invention is to provide the dibutyltin oxide as an aqueous dispersion thereof. However, dibutyltin oxide has proven to be remarkably difficult to formulate into an aqueous dispersion in which the dibutyltin oxide remains homogeneously dispersed in the formulation for any reasonable length of time. Accordingly, there remains a need in this field for aqueous dispersions of dibutyltin oxide wherein the dibutyltin oxide remains homogeneously dispersed for extended periods of time wherein the dispersion is sufficiently fluid that it can be poured and/or pumped, as desired, thereby facilitating its use.

BRIEF SUMMARY OF THE INVENTION

The present invention satisfies these objects and exhibits in addition the advantageous properties described herein.

The invention comprises a homogeneous, stable aqueous dispersion of dibutyltin oxide, comprising (A) about 50 wt. % to about 70 wt. % dibutyltin oxide;

(B) a surfactant component selected from the group consisting of fatty acid ethoxylates of the formula

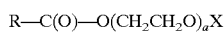

and mixtures thereof, wherein X is H or $R^1$—C(O)—, R is alkyl or alkenyl containing 11 to 23 carbon atoms and 0–5 carbon—carbon double bonds, $R^1$ is alkyl or alkenyl containing 12 to 24 carbon atoms and 0–5 carbon—carbon double bonds, and a is 6 to 12, in an amount from about 1 wt. % to about 5 wt. %;

(C) a suspending agent in an amount from about 0.05% to about 0.15 wt. %;

(D) a viscosity modifier component selected from the group consisting of $C_{12}$–$C_{24}$ fatty acids and alkali metal salts thereof, in an amount from about 0.25 wt. % to about 0.75 wt. %; and (E) water.

Another aspect of the present invention is compositions wherein the aforementioned components (A), (B), (C) and (D) are present in relative amounts in parts by weight of (50–70):(1–5):(0.05–0.15):(0.25–0.75). Such compositions can be anhydrous or can contain water in an amount less than would be present in the finished dispersion described herein. Thus, these compositions can also be termed concentrates. They can be used by adding water to adjust the concentrations to within the ranges described herein for the finished dispersion, and dispersing the components thoroughly as necessary to achieve homogeneity.

Dispersions in accordance with this invention retain their homogeneous state over extended periods of time of several days and longer. The dispersions remain homogeneous liquids, rather than pastes, notwithstanding the significantly high content of dibutyltin oxide in the dispersions. The ability of these dispersions to be handled as liquids, notwithstanding the high dibutyltin oxide content, is a very significant and surprising feature of the present invention.

DETAILED DESCRIPTION OF THE INVENTION

The ability of the dispersions of the present invention to exhibit prolonged homogeneity even at high dibutyltin oxide contents is one of the pronounced and unexpected advantages of this invention. Generally, the dibutyltin oxide content is at least 50 wt. % of the dispersion, and can range as high as about 70 wt. % of the dispersion. A more preferred range of dibutyltin oxide is about 55 wt. % to about 65 wt. % of the dispersion, and more preferably about 57 wt. % to 63 wt. % of the dispersion.

The ability of the dispersion to exhibit the desired homogeneity and fluidity is based on the careful selection of components and the amounts thereof as described herein. One essential component is a surfactant component, comprising one or more compounds of the formula

in which formula X is —H, representing a monoester, or X is $R^1C(O)$—, representing a diester; and R and $R^1$ each represent a straight-chain or branched, preferably straight-chain, alkyl or alkenyl group containing 11–23 carbon atoms (in the case of R) and 12–24 carbon atoms (in the case of $R^1$) and 0–5 carbon—carbon double bonds. Thus, the substituents R and $R^1$ represent the residues of a fatty acid, or a mixture of fatty acids. The symbol a represents the degree of ethoxylation of the ethoxylate of the aforementioned formula. Preferably, a is 6 to 12, and more preferably is 7 to 10. The fatty acid ethoxylates of the aforementioned formula are in many cases commercially available products, and can be synthesized in straightforward manner from the corresponding fatty acids R—COOH (and, optionally, $R^1COOH$) and ethylene oxide.

It will be recognized that the surfactant component may comprise mixtures of different compounds of the aforementioned formula. This is due to the fact that the compounds can be synthesized by esterification of fatty acid R—C(O) OH (and $R^1COOH$ where desired) with polyethylene glycol HO(CH$_2$CH$_2$O)$_a$H, and many commercially available fatty acids are in fact mixtures of various chain lengths representing the natural sources thereof such as tallow, coconut, palm, and the like. Also, polyethylene glycols are often available as mixtures of compounds wherein a represents the mole average chain length.

One example of a preferred surfactant of the aforementioned formula is polyethylene glycol 400 tallate, which is a mixture of polyethylene glycol monoesters of tall oil fatty acid radicals wherein the —(CH$_2$CH$_2$O)$_a$H moiety has an average molecular weight of 400. Other preferred examples include polyethylene glycol laurate, dilaurate, oleate, dioleate, stearate, distearate, and combinations of the above.

The surfactant component generally comprises about 1 wt. % to about 5 wt. % of the aqueous dispersion, more preferably about 2 wt. % to about 4 wt. % thereof. The surfactant is believed to function to help the dibutyltin oxide remain uniformly dispersed in the aqueous medium.

The aqueous dispersions of the present invention also include a suspending agent, to assist in maintaining the dispersion in the desired homogeneous state. The most preferred suspending agent is carrageenan. Other suspending agents performing the equivalent function are also contemplated. The suspending agent should be present in an amount of 0.05 wt. % to 0.15 wt. % of the dispersion, and more preferably about 0.9 to 0.12 wt. % of the dispersion.

The aqueous dispersions of the present invention also include a viscosity modifier component which is effective to help provide the desired relatively fluid state of the dispersion while maintaining its necessary homogeneous condition. Suitable viscosity modifiers include fatty acids containing 12 to 24 carbon atoms and their alkali metal salts. Also contemplated hereby are mixtures of such fatty acids, mixtures of such alkali metal salts of fatty acids, and mixtures of one or more fatty acids with one or more alkali salts thereof. Examples of preferred viscosity modifiers include sodium stearate, isostearic acid, oleic acid, and combinations of two or more thereof. The viscosity modifier component should constitute about 0.25 wt. % to about 0.75 wt. % of the aqueous dispersion, and more preferably about 0.40 wt. % to about 0.60 wt. % thereof.

The aqueous dispersions of the present invention can also include other optional functional additives, for their respective functions, so long as any such additive does not detract from the desired homogeneity, stability and fluidity of the dispersions. One such optional additive that has been found to be useful is a defoamer, in a small but effective amount on the order of 0.1 wt. % of the dispersion. A defoamer assists in the removal of entrained air from the dispersion upon manufacture thereof. Examples of suitable defoaming agents abound in the technology of dispersing inorganic solids in liquid media, and are well known to those of ordinary skill in this art.

The dispersions of the present invention can be made in very straightforward manner by thoroughly mixing together the indicated ingredients in a suitable mixing tank, preferably while the components are heated to temperatures on the order of 45° C. to 75° C. Mixing should be carried out for a time sufficient to provide completely homogeneous dispersion of all components. Mixing times should be at least on the order of 45 minutes, up to several hours or longer. In a preferred embodiment, the water, surfactant and viscosity modifier components and suspending agent are mixed together first, and the dibutyltin oxide is added last in increments depending on the size of the batch being prepared. In this way, the dibutyltin oxide is rapidly and uniformly dispersed into the dispersing system comprising the other components recited herein.

Dispersions prepared in this manner can readily be used to introduce dibutyltin oxide into any manufacturing operation or equipment in which dibutyltin oxide is presently employed in its solid, particulate form. At most modest modification of existing equipment is necessary to accommodate the fluid, liquid state of the dibutyltin oxide dispersion. Indeed, in applications requiring spraying of dibutyltin oxide, the aqueous dispersions of the present invention are quite advantageous in that the liquid suspending vehicle is readily pumpable and sprayable in any existing equipment.

The aqueous dispersions of the present invention thus also provide the ability to dispense dibutyltin oxide in a very easily controllable manner, and do so without requiring the equipment and controls that heretofore have been necessary to deal with the drawbacks which accompany the use of solid finely divided dibutyltin oxide.

As noted, the aqueous dispersions are homogeneous and stable in that they retain their essentially homogeneous state over prolonged periods of time, i.e. several days or longer. Even in those instances when minor amounts of dibutyltin oxide solid begin to separate from the dispersion, this minor amount of dibutyltin oxide can readily be redispersed into the dispersion by gentle agitation in existing equipment, and the thus redispersed material remains dispersed in the composition.

The aqueous dispersions formulated in accordance with this teaching can exhibit viscosities on the order of 3,000 centipoise, or less, in view of which they can be seen to be readily pourable and pumpable, as may be required in the particular applications for these dispersions. Thus, the dispersions can be handled as any other process liquids would be handled.

The present invention will be described further in the following examples. These examples are provided for purposes of description and are not intended to limit the scope of that which is considered to be the invention.

EXAMPLE 1

A dispersion was prepared from the following components:

| Component | Function | Amount (wt. %) |
| --- | --- | --- |
| Polyethylene glycol 400 monotallate | surfactant | 2.83 |
| "Foamknocker 433" | defoamer | 0.08 |
| isostearic acid | viscosity modifier | 0.16 |
| sodium stearate | viscosity modifier | 0.40 |
| carrageenan | suspending agent | 0.11 |
| dibutyltin oxide | active ingredient | 60.14 |
| water | medium | 36.28 |

This dispersion was made by adding the water, polyethylene glycol 400 monotallate, and isostearic acid to a vessel capable of heating its contents up to 60° C. and equipped with an agitator. The mixture was stirred and heated to 60° C. When the temperature had reached 60° C., the sodium stearate and carrageenan were added and mixed in until they were dissolved. The dibutyltin oxide was added in three approximately equal increments, with mixing to homogeneity between each addition. After the last addition of dibutyltin oxide, the mixture was thoroughly mixed for an additional 10 minutes and then was cooled to ambient temperature.

The viscosity of this dispersion after 1 day was 1355 centipoise. The viscosity of this dispersion after 1 month was 1400 centipoise. After storage for 1 month, less than 0.5 wt. % of the solids had settled out of the dispersion.

What is claimed is:

1. A homogeneous, stable aqueous dispersion of dibutyltin oxide, comprising
   (A) about 50 wt. % to about 70 wt. % dibutyltin oxide;
   (B) a surfactant component selected from the group consisting of fatty acid ethoxylates of formula (1)

  (1)

and mixtures thereof, wherein X is —H or $R^1C(O)$—, R is alkyl or alkenyl containing 11 to 23 carbon atoms and 0–5 carbon—carbon double bonds, $R^1$ is alkyl or alkenyl containing 12 to 24 carbon atoms and 0–5 carbon—carbon double bonds, and a is 6 to 12, in an amount from about 1 wt. % to about 5 wt. %;
   (C) a suspending agent in an amount from about 0.05% to about 0.15 wt. %;
   (D) a viscosity modifier component selected from the group consisting of $C_{12}$–$C_{24}$ fatty acids and alkali metal salts thereof, in an amount from about 0.25 wt. % to about 0.75 wt. %; and
   (E) water.

2. A dispersion in accordance with claim 1 wherein in formula (1), X is —H.

3. A dispersion in accordance with claim 2 wherein said suspending agent is carrageenan.

4. A dispersion in accordance with claim 2 wherein a is 7 to 10.

5. A dispersion in accordance with claim 1 wherein in formula (1), X is $R^1C(O)$—.

6. A dispersion in accordance with claim 5 wherein said suspending agent is carrageenan.

7. A dispersion in accordance with claim 5 wherein a is 7 to 10.

8. A composition of matter from which a homogeneous, stable aqueous dispersion of dibutyltin oxide can be produced upon the addition of water thereto, the composition comprising
   (A) dibutyltin oxide;
   (B) a surfactant component selected from the group consisting of fatty acid ethoxylates of formula (1)

  (1)

and mixtures thereof, wherein X is —H or $R^1C(O)$—, R is alkyl or alkenyl containing 11 to 23 carbon atoms and 0–5 carbon—carbon double bonds, $R^1$ is alkyl or alkenyl containing 12 to 24 carbon atoms and 0–5 carbon—carbon double bonds, and a is 6 to 12;
   (C) a suspending agent; and
   (D) a viscosity modifier component selected from the group consisting of $C_{12}$–$C_{24}$ fatty acids and alkali metal salts thereof;
   wherein said components are present in a ratio by parts by weight of (component (A)):(component (B)): (component (C)):(component (D)) of (50–70):(1–5): (0.05–0.15):(0.25–0.75).

9. A composition in accordance with claim 8 wherein in formula (1), X is —H.

10. A composition in accordance with claim 9 wherein said suspending agent is carrageenan.

11. A composition in accordance with claim 9 wherein a is 7 to 13.

12. A composition in accordance with claim 8 wherein in formula (1), X is $R^1C(O)$—.

13. A composition in accordance with claim 12 wherein suspending agent is carrageenan.

14. A composition in accordance with claim 12 wherein a is 7 to 10.

15. A method of forming a homogeneous, stable aqueous dispersion of dibutyltin oxide, comprising dispersing dibutyltin oxide in an amount corresponding to about 50 wt. % to about 70 wt. % of said dispersion in a composition with
   a surfactant component selected from the group consisting of fatty acid ethoxylates of formula (1)

  (1)

and mixtures thereof, wherein X is —H or $R^1C(O)$—, R is alkyl or alkenyl containing 11 to 23 carbon atoms and 0–5 carbon—carbon double bonds, $R^1$ is alkyl or alkenyl containing 12 to 24 carbon atoms and 0–5 carbon—carbon double bonds, and a is 6 to 12, in an an amount from about 1 wt. % to about 5 wt. % of said dispersion,
   a suspending agent in an in an amount from about 0.05% to about 0.15 wt. % of said dispersion,
   a viscosity modifier component selected from the group consisting of $C_{12}$–$C_{24}$ fatty acids and alkali metal salts thereof, in an in an amount from about 0.25 wt. % to about 0.75 wt. % of said dispersion, and
   water.

16. A method in an accordance with claim 15 wherein in an formula (1), X is —H.

17. A method in an accordance with claim 16 wherein said suspending agent is carrageenan.

18. A method in an accordance with claim 16 wherein a is 7 to 10.

19. A method in an accordance with claim 15 wherein in formula (1), X is $R^1C(O)$—.

20. A method in an accordance with claim 19 wherein said suspending agent is carrageenan.

21. A method in an accordance with claim 19 wherein a is 7 to 10.

* * * * *

UNITED STATES PATENT AND TRADEMARK OFFICE
CERTIFICATE OF CORRECTION

PATENT NO. : 5,807,802
DATED : August 24, 2000
INVENTOR(S) : Rosemarie E. Stewart, et al.

It is certified that error appears in the above-identified patent and that said Letters Patent is hereby corrected as shown below:

Column 6,
Line 13, "7 to 13" should read -- 7 to 10 --
Line 34, "in an an amount" should read -- in an amount --
Line 37, "in an an amount" should read -- in an amount --
Line 42, "in an an amount" should read -- in an amount --

Signed and Sealed this

Twenty-first Day of August, 2001

Attest:

Nicholas P. Godici

*Attesting Officer*

NICHOLAS P. GODICI
*Acting Director of the United States Patent and Trademark Office*